US010182717B2

(12) United States Patent
Lindig et al.

(10) Patent No.: US 10,182,717 B2
(45) Date of Patent: *Jan. 22, 2019

(54) SYSTEMS FOR DETERMINING EYE REFRACTION

(71) Applicants: Carl Zeiss AG, Oberkochen (DE); Carl Zeiss Vision International GmbH, Aalen (DE)

(72) Inventors: Karsten Lindig, Erfurt (DE); Jesús-Miguel Cabeza-Guillén, Aalen (DE)

(73) Assignees: Carl Zeiss AG, Oberkochen (DE); Carl Zeiss Vision International GmbH, Aalen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/430,514

(22) Filed: Feb. 12, 2017

(65) Prior Publication Data

US 2017/0150882 A1 Jun. 1, 2017

Related U.S. Application Data

(63) Continuation of application No. PCT/EP2015/071690, filed on Sep. 22, 2015.

(30) Foreign Application Priority Data

Sep. 22, 2014 (DE) .......................... 10 2014 113 680
Nov. 14, 2014 (DE) .......................... 10 2014 116 665

(51) Int. Cl.
*A61B 3/10* (2006.01)
*A61B 3/14* (2006.01)
(Continued)

(52) U.S. Cl.
CPC .............. *A61B 3/032* (2013.01); *A61B 3/005* (2013.01); *A61B 3/0008* (2013.01);
(Continued)

(58) Field of Classification Search
CPC .. A61B 3/04; A61B 3/103; A61B 3/14; A61B 3/152; A61B 3/113; A61B 3/1225;
(Continued)

(56) References Cited

U.S. PATENT DOCUMENTS 7,963,652 B2 6/2011 Vertegaal et al.
8,403,480 B2 3/2013 Chen et al.
(Continued)

FOREIGN PATENT DOCUMENTS

DE 4326760 A1 3/1995
DE 10348854 A1 5/2005
(Continued)

OTHER PUBLICATIONS

Liu, Changmeng, and Mark D. Fairchild. "Measuring the relationship between perceived image contrast and surround illumination." Color and Imaging Conference. vol. 2004. No. 1. Society for Imaging Science and Technology, 2004.*

(Continued)

*Primary Examiner* — Dawayne A Pinkney
(74) *Attorney, Agent, or Firm* — Walter Ottesen, P.A.

(57) ABSTRACT

Mobile computer devices and systems for refraction determination of an eye, for example for objective refraction determination and/or subjective refraction determination, are provided. Here, a display of the mobile computer device can be driven to display an image for refraction determination.

7 Claims, 10 Drawing Sheets

(51) Int. Cl.
*A61B 3/00* (2006.01)
*A61B 3/032* (2006.01)
*A61B 3/103* (2006.01)
*G02C 7/02* (2006.01)
*A61B 3/04* (2006.01)
*A61B 3/06* (2006.01)
*A61B 3/11* (2006.01)
*A61B 5/00* (2006.01)
*A61B 3/113* (2006.01)

(52) U.S. Cl.
CPC .......... *A61B 3/0025* (2013.01); *A61B 3/0041* (2013.01); *A61B 3/04* (2013.01); *A61B 3/063* (2013.01); *A61B 3/103* (2013.01); *A61B 3/112* (2013.01); *A61B 3/113* (2013.01); *A61B 3/14* (2013.01); *A61B 5/6898* (2013.01); *G02C 7/024* (2013.01); *G02C 7/028* (2013.01); *A61B 3/10* (2013.01)

(58) Field of Classification Search
CPC ....... A61B 3/024; A61B 3/032; A61B 3/0285; A61B 3/18; A61B 3/1015; A61H 5/00
USPC ........ 351/228, 200, 203, 205–206, 208–210, 351/216, 221–223, 227, 230–231, 351/233–234, 236, 240, 245–246
See application file for complete search history.

(56) References Cited

U.S. PATENT DOCUMENTS

| | | | |
|---|---|---|---|
| 8,708,490 B2 | 4/2014 | Baranton et al. | |
| 8,783,871 B2 | 7/2014 | Pamplona et al. | |
| 8,931,905 B2 | 1/2015 | Lewis | |
| 9,186,293 B2 | 11/2015 | Krenik | |
| 9,237,842 B2 | 1/2016 | Lee et al. | |
| 9,237,846 B2 | 1/2016 | Mowrey et al. | |
| 9,380,938 B2 | 7/2016 | Huang et al. | |
| 2003/0108350 A1 | 6/2003 | Brauning | |
| 2007/0008493 A1 | 1/2007 | Kratzer | |
| 2009/0153796 A1 | 6/2009 | Rabner | |
| 2011/0176106 A1 | 7/2011 | Lewkowski | |
| 2013/0027668 A1 | 1/2013 | Pamplona et al. | |
| 2013/0083185 A1 | 4/2013 | Coleman, III | |
| 2013/0170017 A1* | 7/2013 | Caldeira | G02B 25/001 359/319 |
| 2015/0150444 A1 | 6/2015 | Bex et al. | |
| 2016/0157716 A1* | 6/2016 | Pamplona | A61B 3/18 351/213 |

FOREIGN PATENT DOCUMENTS

| | | |
|---|---|---|
| DE | 102008012268 A1 | 9/2009 |
| DE | 202011103183 U1 | 9/2011 |
| WO | 2013036629 A2 | 3/2013 |
| WO | 2013170091 A1 | 11/2013 |

OTHER PUBLICATIONS

English translation of the Office action of the German Patent Office dated Jun. 26, 2015 in German patent application 10 2014 116 665.5 on which a claim of priority is based.

International Search Report of the international searching authority dated Nov. 18, 2015 in international patent application PCT/EP2015/071690 on which the claim of priority is based.

English translation and International Preliminary Report on Patentability dated Dec. 19, 2016 in international patent application PCT/EP2015/071690 on which the claim of priority is based.

* cited by examiner

SYSTEMS FOR DETERMINING EYE REFRACTION

CROSS REFERENCE TO RELATED APPLICATION

This application is a continuation application of international patent application PCT/EP2015/071690, filed Sep. 22, 2015, designating the United States and claiming priority from German applications 10 2014 113 680.2, filed Sep. 22, 2014 and 10 2014 116 665.5 filed Nov. 14, 2014, and the entire content of the above applications is incorporated herein by reference.

FIELD OF THE INVENTION

The present application relates to methods, devices and systems for determining eye refraction and corresponding computer program products. In this case, eye refraction should be understood to mean a determination of a refraction of one or both eyes of a living being, in particular of a human being. In this case, values for sphere (in dioptres), cylinder and axis are usually determined. Such a determination of eye refraction is used, for example, to adapt visual aids such as eyeglasses or contact lenses to a respective person.

BACKGROUND OF THE INVENTION

In the field of medicine, conventional diagnosis systems for determining eye refraction are generally embodied as individual table top systems. In this case, for example, an autorefractor or an oscilloscope is used for objectively determining eye refraction. Besides the objective refraction determination by means of such apparatuses in which an objective measurement of the refraction of the eye is effected, so-called subjective refraction determinations are often carried out as well, in which different lenses or other optical elements having different optical properties are provided for a person (for example in an eyeglasses frame with a mount for such lenses) and the person indicates whether a visual impression improves or deteriorates. For this purpose, the person usually views an eye chart containing characters or symbols that is situated at a relatively large distance, for example 4 m.

Consequently, a relatively large amount of space is conventionally required for determining eye refraction. Moreover, devices necessary for this purpose are often relatively expensive. Therefore, it is desirable to provide more compact devices for determining eye refraction.

US 2013/0235346 A1 discloses using a smartphone or other computer units for eye examination, in particular for photorefraction. In this case, a camera of the smartphone is used to record one eye or both eyes of a person to be examined, and an illumination is provided for example via a flash or other lighting unit of the smartphone.

US 2012/0212598 A1 discloses illuminating an eye to be examined by means of a light emitting diode arrangement in order to be able to illuminate an eye from different directions. Thus, a specialized apparatus is again provided here which, under certain circumstances, is comparatively expensive.

DE 10153397 A1 discloses further methods and devices for measuring the refraction of an eye in which an eye is illuminated and then an image of the eye is evaluated.

US 2013/0027668 A1 discloses a method for subjective refraction determination, for which a mobile display device, in particular a smartphone, can be used. In this case, images are displayed which have to be made congruent by a subject.

DE 10 2008 012 268 A1 discloses a stationary device for objective refraction determination.

US 2006/0110008A1 discloses methods and devices for calibration-free eye gaze tracking.

DE 20 2011 103 183 U1 discloses an image separator which can be attached to a tablet computer for determining deficiencies in the visual acuity and refraction of an eye.

SUMMARY OF THE INVENTION

Proceeding therefrom it is an object of the present invention to provide devices, systems and computer program products for determining eye refraction which, for example, compared with more conventional procedures, are more cost-effective to implement and/or afford an increased accuracy and/or are usable more flexibly than conventional stationary units.

In accordance with a first aspect, a mobile computer device is provided, including a display, a processor, and a memory with program code stored therein, wherein the program code, when it is executed on the processor, has the effect that the processor drives the display to display an image (that is one image or a plurality of successive images) for determining the refraction of an eye on the display.

In this case, the image includes elements represented on a background, wherein a brightness of the background is settable for setting a surround luminance, in particular an adaptation luminance. The first aspect is characterized in that the brightness of the background is selectively settable to one of at least two different predefined brightness values, wherein the at least two different predefined brightness values are from a group including a first predefined brightness value with a first luminance of less than $0.03$ $cd/m^2$, a second predefined brightness value with a second luminance of greater than $3$ $cd/m^2$ and a third brightness value with a third luminance between the first luminance and the second luminance.

In this case, the first luminance is in the range of scotopic vision, the second luminance is in the range of photopic vision and the third luminance is in the range of mesopic vision.

Photoptic vision, also called daytime vision or cone vision, denotes the vision of a human being when there is sufficient brightness. This is contrasted with scotopic vision, also called night vision or rod vision, when there is low brightness, and the transition range, the mesopic range or twilight vision. Scotopic vision typically occurs from the perception threshold up to a luminance of approximately $0.003$-$0.03$ $cd/m^2$. The range of mesopic vision is above that up to luminances of approximately $3$-$30$ $cd/m^2$. Photopic vision occurs at even higher luminances. In accordance with the first aspect, therefore, the brightness of the background can selectively be set to at least two of these three ranges in order to carry out a refraction determination in the corresponding visual range (photopic, scotopic or mesopic). In this way, a single device can be used to carry out the refraction determination in different ranges of vision.

In addition, a brightness of the elements may be settable for setting an infield luminance.

In accordance with a second aspect, a mobile computer device is provided, including a display, a processor, and a memory with program code stored therein, wherein the program code, when it is executed on the processor, has the effect that the processor drives the display to display an image (that is one image or a plurality of successive images) for determining the refraction of an eye on the display.

In this case, the image includes elements represented on a background, wherein a brightness of the background is settable for setting a surround luminance. In addition, that is independently thereof, in the case of the second aspect, a brightness of the elements is settable for setting an infield luminance.

In this case, as usual in optics, the infield luminance is the average luminance of all the objects situated in the infield. In this case, the infield is generally the area of a viewed visual object as a position within the entire field of view. For such a visual object the infield is generally situated in the principal viewing direction of the corresponding eye and its size is determined by the size of the visual object in the case of small viewing movements. It is generally not greater than 20° and is surrounded by the surround. The surround luminance is then correspondingly the average luminance of the surround.

This provides a high flexibility in the setting of a contrast between elements and background and also in a setting of an adaptation luminance which determines eye adaptation.

In the case of the first or second aspect, the image may include an image for the subjective refraction determination, wherein the image includes characters and/or symbols, for example.

The image may also include a structured illumination for illuminating the eye for an objective refraction determination. In this case, a structured illumination is an illumination which, in contrast to a uniform illumination, has a spatial structure, in particular a pattern (which corresponds to a spatial change in the brightness and/or the color) or a different type of spatial modulation.

The structured illumination may be temporally variable in order in particular to illuminate the eye from different directions. By way of example, for this purpose, different parts of a pattern may be successively switched to "bright", while other parts of the pattern remain dark. As a result, the eye can be examined with illumination from different directions.

In this case, the structured illumination may include selectively drivable, circularly arranged light source points or ring segments.

The mobile computer device may further include a camera unit for recording a pupillary light reflex in response to the structured illumination.

Additionally or alternatively, the mobile computer device may include an interface for coupling to an external camera and for receiving a recorded pupillary light reflex in response to the structured illumination from the external camera.

The program code, when it is executed on the processor, may then carry out a determination of the refraction of the eye on the basis of the recorded pupillary light reflex.

In accordance with a third aspect, a mobile computer device is provided, the mobile computer device including:
 a display,
 a processor, and
 a memory with program code stored therein,
wherein the program code, when it is executed on the processor, has the effect that the processor drives the display to display an image for determining the refraction of an eye on the display, wherein the image includes a structured illumination for illuminating the eye for an objective refraction determination, further including a camera unit for recording a pupillary light reflex in response to the structured illumination and/or an interface for coupling to an external camera and for receiving a recorded pupillary light reflex in response to the structured illumination from the external camera, characterized in that the program code, when it is executed on the processor, carries out a determination of the refraction of the eye on the basis of the recorded pupillary light reflex.

In this way, compared with conventional stationary devices, it is possible to carry out an objective refraction determination with a mobile computer device, which increases a flexibility in use. In particular, such a device can easily be carried.

In accordance with a fourth aspect, a system is provided, the system including:
 a mobile computer device, comprising:
  a display,
  a processor, and
  a memory with program code stored therein,
 wherein the program code, when it is executed on the processor, has the effect that the processor drives the display to display an image for determining the refraction of an eye on the display, and
viewing optics for viewing the mobile computer device with at least one eye of a person to be examined,
characterized in that a changeable mount for a changeable optical unit for the subjective refraction determination is present.

A subjective refraction determination in which a subject views the image successively through different changeable optical units (for example, having different refractive powers) is thereby possible in a simple manner with the aid of a mobile computer device.

The changeable mount may be configured in particular for receiving changeable lenses, and/or changeable lenses may be received in the changeable mount. The system may include the changeable lenses. As a result, a subject may view the represented image through different changeable lenses, and properties of that changeable lens which offers subjectively the best image impression may then be used for example as a basis for manufacturing an eyeglass lens or for choosing a contact lens.

In accordance with a fifth aspect, a system is provided, including a mobile computer device as described above, and viewing optics for viewing the mobile computer device with at least one eye of a person to be examined.

The viewing optics may include a first optical unit for a first eye and a second optical unit for a second eye in order to enable binocular viewing and/or examination.

Additionally or alternatively, the viewing optics may include a microlens arrangement. In this case, a microlens arrangement is an arrangement of a multiplicity of microlenses (that is small lenses), which can be provided for example in a two dimensional arrangement in rows and columns.

The microlens arrangement may include in particular a microlens film to be fitted on the display of the mobile computer device. A compact construction is thus possible.

The viewing optics may also include a color filter. In this case, the color filter may include a red filter and/or infrared filter. What may be achieved as a result is that from the displayed image only light of the wavelengths selected by the filter reaches the eye. In this case, particularly red light or infrared light has a smaller influence on the adaptation of the pupil, such that it is possible to work for example with a comparatively high light intensity and nevertheless a comparatively large pupil.

The system may further include a beam splitter arranged between the display of the mobile computer device and the at least one eye, wherein the beam splitter is arranged to direct light emerging from the eye to a camera unit.

The system of the fifth aspect may additionally include a changeable mount for a changeable optical unit for the subjective refraction determination.

The system may further comprise, for at least one eye, a combination of polarizer and analyzer. For the at least one eye it is thereby possible to suppress extraneous light, for example from a channel for another eye.

The system may further comprise, for at least one eye, a shutter.

In accordance with a sixth aspect, a method for eye examination is provided, the method including:
displaying an image for determining the refraction of an eye on a display of a mobile computer device, wherein the image includes elements represented on a background, and
setting a brightness of the background for setting a surround luminance,
wherein the brightness of the background is selectively set for the refraction determination for at least two types of vision from the group including scotopic vision, photopic vision and mesopic vision.

As in the case of the first aspect, a refraction determination for different visual ranges (scotopic, photopic, mesopic) is thus possible in a simple manner.

In the case of the method of the sixth aspect, the brightness of the background for scotopic vision may have a luminance of less than 0.03 $cd/m^2$ and the brightness of the background for photopic vision may have a luminance of greater than 3 $cd/m^2$.

In a manner similar to the first aspect, in the case of the sixth aspect, setting the brightness of the background may include selectively setting the brightness to one of at least two different predefined brightness values, wherein the at least two different predefined brightness values are from a group including a first predefined brightness value with a first luminance of less than 0.03 $cd/m^2$, a second predefined brightness value with a second luminance of greater than 3 $cd/m^2$ and a third brightness value with a third luminance between the first luminance and the second luminance.

The method may further include:
setting a brightness of the elements for setting an infield luminance.

In accordance with a seventh aspect, a method for eye examination is provided, including:
displaying an image for determining the refraction of an eye on a display of a mobile computer device, wherein the image includes elements represented on a background,
setting a brightness of the background for setting a surround luminance, and
additionally, that is independently thereof, setting a brightness of the elements for setting an infield luminance.

The terms infield luminance and surround luminance should be understood here as usual in optics and as explained for the first and second aspects.

In the methods, the image may include a structured illumination for illuminating the eye for an objective refraction determination.

In this case, a structured illumination is an illumination which, in contrast to a uniform illumination, has a spatial structure, in particular a pattern (which corresponds to a spatial change in the brightness and/or the color) or a different type of spatial modulation.

The methods may then further include:
temporally varying the structured illumination in order to illuminate the eye from different directions. By way of example, for this purpose, different parts of a pattern may be successively switched to "bright", while other parts of the pattern remain dark. As a result, the eye can be examined with illumination from different directions.

The methods may further include recording a pupillary light reflex in response to the structured illumination. The pupillary light reflex may give indications of properties of the eye such as viewing direction or refraction.

The methods may further include carrying out a determination of the refraction of the eye on the basis of the recorded pupillary light reflex by means of a program code executed on a processor of the mobile computer device. In this case, the refraction determination may be effected on the basis of a change in a position of the reflex in the case of a change in the structured illumination, as will be explained in even greater detail later.

In accordance with a seventh aspect, a method for eye examination is provided, including:
displaying an image for determining the refraction of an eye on a display of a mobile computer device, wherein the image includes a structured illumination for illuminating the eye for an objective refraction determination,
recording a pupillary light reflex in response to the structured illumination,
characterized by
carrying out a determination of the refraction of the eye on the basis of the recorded pupillary light reflex by means of a program code executed on a processor of the mobile computer device (10; 20; 60).

In accordance with an eighth aspect, a computer program product is provided which is loadable into a memory of a mobile computer device, including software code which performs one of the methods described above when it is executed on the mobile computer device. The computer program product may be for example a physical medium on which the software code is provided, for example a memory card, a USB stick, a DVD-ROM, a CD-ROM or some other type of memory. However, signals or the like with which the software code is provided may also be involved.

Consequently, according to the invention, both an objective refraction measurement and a subjective refraction measurement are possible by means of a mobile computer device, in particular a smartphone or a tablet. In this case, the above-described techniques, devices and methods for objective refraction measurement and for subjective refraction measurement may be combined in a single device, but separate devices may likewise also be provided.

BRIEF DESCRIPTION OF THE DRAWINGS

The invention will now be described with reference to the drawings wherein.

DESCRIPTION OF THE PREFERRED EMBODIMENTS OF THE INVENTION

Various embodiments of the present invention are explained in detail below with reference to the accompanying drawings. These embodiments serve merely for illustration and should not be interpreted as restrictive. By way of example, a description of an embodiment with a multiplicity of elements or features does not mean that all of the elements or features are necessary for implementing embodiments. Rather, other embodiments may have fewer features or elements, alternative features or elements and/or additional features or elements. Moreover, features or elements of different embodiments may be combined with one another, unless indicated otherwise.

Figure 1:
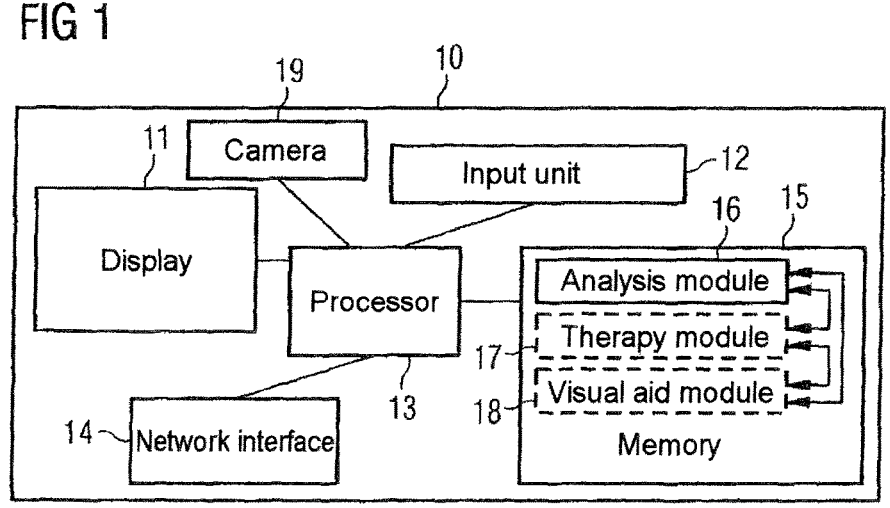
FIG. 1 is a block diagram of a mobile computer device in accordance with one embodiment.

FIG. 1 illustrates a mobile computer device 10 in accordance with one embodiment. The mobile computer device 10 may be implemented for example by means of a smartphone, a tablet computer or by means of some other mobile computer device (for example a mobile gaming device). Such mobile computer devices which may serve as a basis for the implementation of the mobile computer device 10 in FIG. 1 are often freely programmable, and have a processor, a display (if appropriate touch sensitive), various input units, network interfaces, et cetera. As explained in greater detail below, in embodiments of the present invention, such mobile computer devices are used to provide possibilities for refraction determination. For this purpose, in particular, the mobile computer device may be correspondingly programmed, for example by means of one or more so called apps (from "applications", that is application programs).

As an example, the mobile computer device in FIG. 1 includes a processor 13, for example a CPU. In other embodiments, a plurality of processors or a processor having a plurality of processor cores may also be provided. The processor 13 is coupled to a memory 15, for example a random access memory (RAM) or a nonvolatile memory such as a flash memory, or combinations thereof. Data and also programs for operating the processor 13 and the mobile computer device 10 may be stored in the memory 15. In particular, various application programs (apps) may be stored in the memory 15, for example application program modules 16 and 17, which are discussed in greater detail later.

The processor 13 is further coupled to a display 11, via which images, for example information, graphics, characters, symbols and the like may be represented for viewing by a user. The term "image" is used generally here to denote contents which are represented on a display. Such an image may include for example characters, symbols and/or other elements. Furthermore, the processor 13 is coupled to an input unit 12. In some embodiments, the display 11 may be touch-sensitive and thus simultaneously constitute the input unit 12 or a part thereof. Additionally or alternatively, the input unit may include buttons, rotary controllers, a keyboard, a microphone for receiving sounds or voice input and/or sensors such as an inclination sensor or an acceleration sensor.

Furthermore, in the embodiment in FIG. 1, the mobile computer device 10 includes one or more cameras 19. By way of example, modern smartphones typically have at least one front camera situated on the same side as the display 11, and also a rear camera on the opposite side, wherein in many cases the rear camera offers a higher resolution. However, other configurations are also possible. In some embodiments, a camera of this type, such as the camera 19, is used to record an image of one or both eyes of a user in order to carry out an objective refraction determination on the basis thereof. In other embodiments, an external camera may be used for this purpose.

Furthermore, the mobile computer device 10 in FIG. 1 includes a network interface 14, by means of which the computer device 10 may communicate with further devices. The network interface 14 may include for example a mobile radio interface for communication via a mobile radio network, a Bluetooth interface and/or a Wifi-WLAN interface, but is not restricted thereto. Such a network interface 14 may serve for example for communication with one or more external camera(s), for example via Bluetooth. Such an external camera may, as will be explained in greater detail later, likewise serve for recording one or both eyes of a user. It should be noted that the mobile computer device 10 may include further conventional components of mobile computer devices such as smartphones, for example.

In the embodiment illustrated, an analysis module 16 for refraction determination and selectively additionally a further module 17 are stored as application programs in the memory 15.

As indicated by arrows, the modules may also interact with one another, in particular exchange data. The analysis module 16 serves to carry out a refraction determination by means of the mobile computer device. By way of example, for objective refraction determination with an internal camera such as the camera 19 in FIG. 1 or an external camera coupled to the mobile computer device, images of one or both eyes of a user may be recorded, and the images may be evaluated. In addition, for this purpose the display such as the display 11 may be driven to represent one or more images which form an illumination for the eye or eyes, in particular a structured illumination. In this case, a structured illumination may be in particular an illumination with a predefined, if appropriate, variable pattern.

Moreover, the display 11 may be driven to display images, for example symbols, for example characters or numbers, for carrying out a subjective refraction determination. This may be effected with variable background brightness in some embodiments.

Moreover, a further module 17 may selectively be provided, which may exchange data with the analysis module. The further module 17 may provide for example order functions for visual aids on the basis of the eye refraction determined or else, if appropriate, therapy and/or visual aid functions.

Moreover, via the further module 17, for example, it is also possible to communicate the results via the network interface 14 for example to an ophthalmologist or other medical specialist personnel.

It should be noted that in some embodiments the analysis module 16 may also perform only partial tasks of the refraction determination. By way of example, raw data may also be transmitted to a further computer device, and the recorded data (for example images) may be evaluated there.

With such a mobile computer device, embodiments and measurements are possible under controlled lighting conditions. Refraction determinations can thus be carried out with different adaptation levels and hence different pupil sizes. Moreover, many displays of present day smartphones or tablets have a high dynamic range. This enables illuminations for analysis with a very high contrast range. By way of example, displays on the basis of organic light emitting diodes (OLEDs) have a contrast range of 1000:1 or more, which may be helpful for providing an illumination for the eye.

Figure 2:
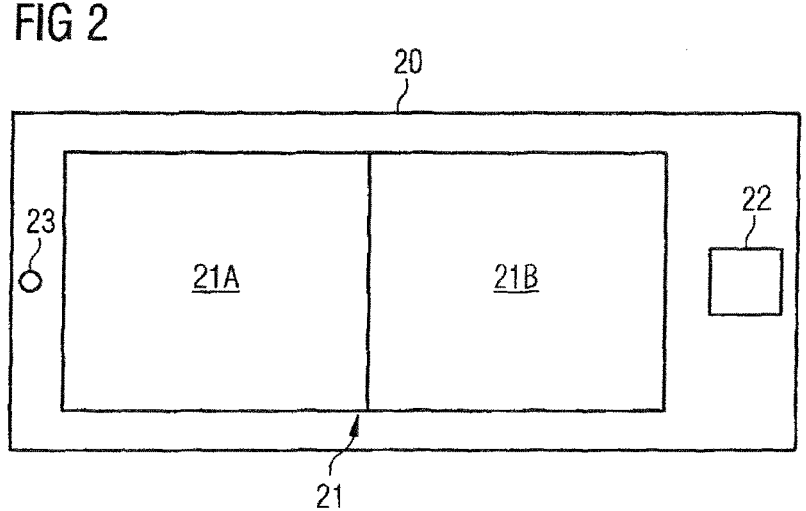
FIG. 2 is a schematic exterior view of a mobile computer device in accordance with one embodiment.

FIG. 2 illustrates one example of an exterior view of a mobile device 20 in accordance with one embodiment of the present invention. The mobile device 20 in FIG. 2 may correspond for example to the mobile computer device 10 in FIG. 1 and is configured as a smartphone in the example in FIG. 2. Depending on the type of smartphone, the exterior view may differ from that illustrated in FIG. 2. The mobile computer device 20 includes a display 21, which may be realized in particular as a touch-sensitive display (so-called touch screen). Moreover, in the example illustrated, the mobile computer device 20 includes an operating button 22 and also a camera 23. The camera 23 is also referred to as front camera. A further camera (not illustrated in FIG. 2) may be situated on the opposite side (rear side) of the mobile computer device 20. The mobile computer device 20 may include further elements not illustrated in FIG. 2, such as, for example, a headphones output, further operating elements, a loudspeaker or a microphone.

As illustrated in FIG. 2, the display 21 may be subdivided into two regions 21A and 21B. In this case, for example, the region 21A may be used for representing an image and/or an illumination for a left eye of a user, and the region 21B for representing an image and/or illumination for a right eye of a user. As will be explained in greater detail below, the mobile computer device 20 can be inserted into a corresponding viewing device.

As a result of the display being divided as illustrated in FIG. 2, left and right eyes may be tested separately for example by the analysis module 16, for example by something being displayed only in the region 21A or only in the region 21B and corresponding feedback from a user being evaluated, or stereo visual capabilities and the like may be tested.

In the regions 21A and 21B, for example, images for left and right eyes may be represented in accordance with a pupilary distance in order to enable stereo viewing. By way of example, a distance between corresponding points may be adapted such that it corresponds approximately to the pupilary distance of an adult human being, for example approximately 65 mm. In some embodiments, the pupilary distance may also be a parameter, such that the representation can be adapted to a respective user and the pupilary distance thereof.

Mobile computer devices as illustrated in FIGS. 1 and 2 are often comparatively cost-effective since they are produced in large numbers. Nevertheless, high-quality displays, cameras, sensors, et cetera are often used in such devices.

Figure 3:
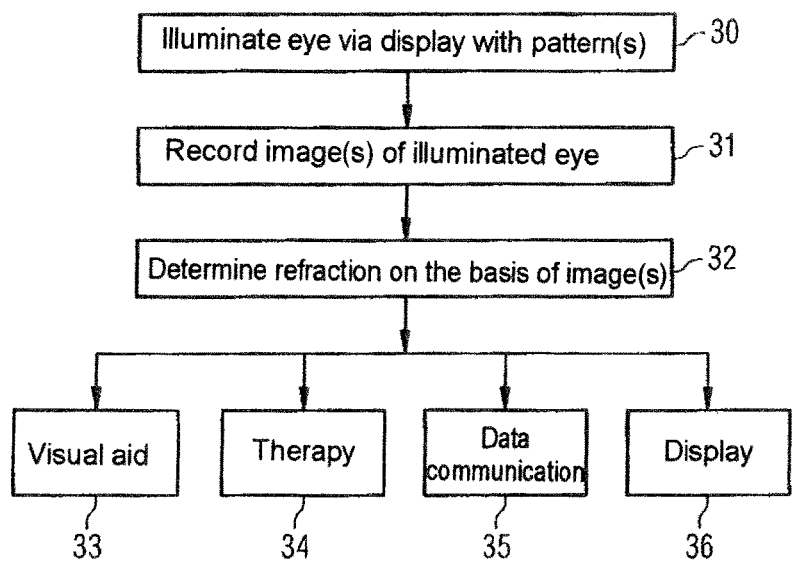
FIG. 3 is a flow diagram for illustrating the functioning of mobile computer devices in accordance with embodiments.

FIG. 3 illustrates a flow diagram for illustrating a method for objective refraction determination. The method may be implemented for example by the analysis module 16 in FIG. 1 by means of a mobile computer device such as the mobile computer device 10 in FIG. 1.

For simplification, only one eye is mentioned here in the description of FIG. 3. However, the various steps in FIG. 3 are applicable to both eyes, one after the other or simultaneously. "An" in "an eye" should thus be understood as the indefinite article and not as a restrictive numerical indication.

In a step 30, an eye of a user is illuminated via a display of a mobile computer device (for example display 11 in FIG. 1 or display 21 in FIG. 2) with a pattern that may vary in particular temporally. In step 31, images of the illuminated eye are then correspondingly recorded.

In step 32, the eye refraction is determined on the basis of the images. This may be done in principle as in the devices mentioned in the introduction which use an illumination from different directions, wherein the display of the smartphone serves as illumination in the embodiment in FIG. 3.

The eye refraction thus determined may be used in various ways, as indicated by way of example by steps 33 to 36 in FIG. 3. Steps 33 to 36 may be implemented independently of one another and, in other embodiments, may also be wholly or partly omitted.

By way of example, in step 33 the eye refraction determined is used to correspondingly adapt a visual aid (for example eyeglasses or contact lenses). In step 34 the refraction determined is used as a basis for a therapy. In step 35 a data communication takes place, for example to medical specialist personnel such as a physician or an optician. By way of example, if the refraction were determined, corresponding data may be communicated to an optician who may then provide corresponding eyeglasses. A data communication is also possible directly to an eyeglasses manufacturer or eyeglass lens manufacturer, for example, which may then provide corresponding eyeglasses or eyeglass lenses. Prior to such an order, a corresponding query may be arranged with a user and/or medicinal specialist personnel. Finally, the eye refraction determined may also simply be displayed in step 36, or on the basis of the eye refraction a recommendation may be expressed on a display, for example a recommendation to visit an ophthalmologist.

As already explained, determining refraction of an eye (or both eyes) of a user, that is of a person to be examined, may be illuminated in a structured fashion. In particular, an illumination may be effected sequentially from different directions, similarly to the prior art discussed in the introduction, wherein in embodiments of the invention, in contrast to the prior art discussed, the illumination is effected with the aid of a display of a mobile computer device, such as a smartphone, for example, and not by means of discrete light sources such as light emitting diodes. Examples of such an illumination will now be explained in greater detail with reference to FIGS. 4 and 5.

Figure 4:
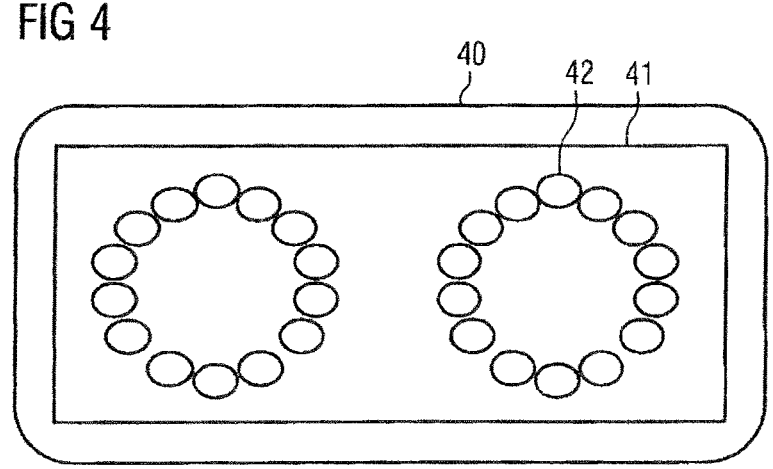
FIG. 4 is an illustration of a possible structured illumination for carrying out an objective refraction determination in accordance with one embodiment.

As a first example, FIG. 4 illustrates a mobile computer device 40, for example a smartphone or a tablet computer, including a display 41. In FIG. 4, light source points 42 each forming a settable ring illumination in order to illuminate the respective eye from different directions may be represented separately for left and right eyes on the display 41. In this case, the individual light source points 42 could be activated sequentially or else in groups, for example, in order thus to illuminate the eye from a respective direction depending on the activated light source point 42. In this case, the luminance level of the light source points 42 may be settable, that is the brightness of the light source points 42 may be variable as required within the possibilities afforded by the display 41. The color may also be settable.

Moreover, a surround luminance L u may also be settable, that is the background (that part of the display 41 which does not serve to represent a currently active point wave 42) may likewise be settable. In this case, the light source points 42 in FIG. 4 are for example circles of a specific size, that is, not points in the mathematical sense, and may approximately serve as point light sources.

Figure 5:
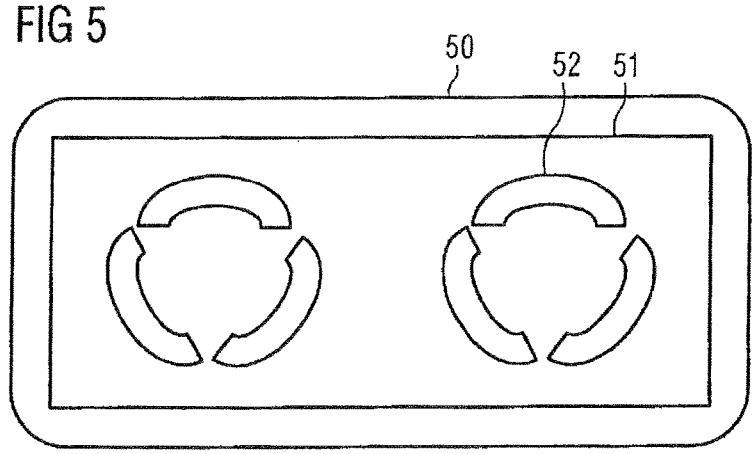
FIG. 5 shows an alternative to the structured illumination from FIG. 4.

The illumination with light source points in FIG. 4 serves merely as an example, and other illuminations are also possible. In this regard, FIG. 5 shows a further possibility. Here ring segments 52 are displayed on a display 51 of a mobile computer device 50, which ring segments are activatable and deactivatable either individually or in groups. As in the embodiment in FIG. 4, in FIG. 5 as well both a luminance of the circle segments 52 and a background luminance (surround luminance) may be settable.

Other shapes are also possible. By way of example, concentric rings of different sizes may likewise serve as structured illumination, or individual points, which may also move on the display. FIGS. 4 and 5 respectively illustrate point waves 42 and ring segments 52 for left and right eyes. In this case, the display is split as explained with reference to FIG. 2. In other embodiments, the display may also be used only for representing an illumination for one eye. In this case, for example, the position of the mobile computer device 50 may be varied depending on the eye to be examined.

By varying the luminances, in particular scotopic vision (also referred to as night vision or rod vision), phototopic vision (also referred to as daytime vision or cone vision) and the transition range therebetween (mesopic vision or twilight vision) may be examined separately.

Various systems in accordance with embodiments in which an objective refraction determination can be carried out by means of a mobile computer device such as a smartphone will be discussed next. Various variants of these systems will be explained with reference to FIGS. 6 to 12. In order to avoid repetitions, identical or mutually corresponding elements here are identified by the same reference signs and will not be explained repeatedly.

Figure 6:
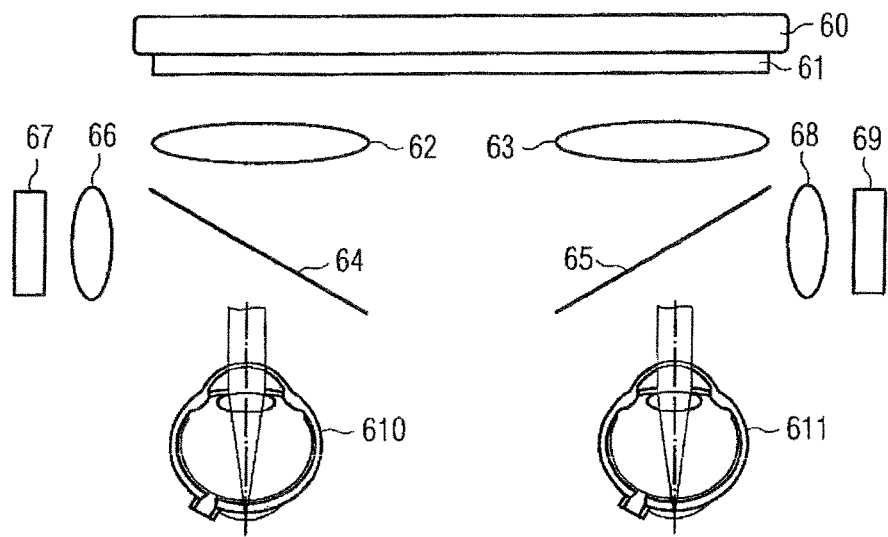
FIGS. 6 to 12 show various variants of systems for objective refraction determination in accordance with various embodiments.

A first embodiment is illustrated in FIG. 6. In this case, the system in FIG. 6 includes a mobile computer device 60, for example a smartphone or tablet, including a display 61, which serves for representing a structured illumination for a left eye 610 and a right eye 611 of a user. In this case, the mobile computer device 60 may be configured as discussed with reference to FIGS. 1 and 2, may perform the functions discussed with reference to FIG. 3 and/or may provide the illumination discussed with reference to FIGS. 4 and 5.

In FIG. 6, the mobile computer device 60 is provided for example in a mount in which the other components illustrated in FIG. 6 are also provided or are coupled thereto. Such a mount may be worn for example on the head (for example as a so-called head-mounted display, HMD).

In the embodiment in FIG. 6, the system further includes optical units 62, 63 for imaging an image concerning the left eye 610 and the right eye 611, respectively, the image being represented on the display 61. As discussed above, the optical units 62, 63 may be provided for example in a viewing device such as a head-mounted display. While the optical units 62, 63 are illustrated as individual lenses for simplification in FIG. 6, the optical units 62, 63 may also include in each case a plurality of optical elements, for example lenses.

A first camera unit including an image sensor 67, for example a CMOS sensor or a CCD sensor, and including a camera optical unit 66 is provided for recording an image of the left eye 610. In a corresponding manner, a second camera unit including an image sensor 69 and including a camera optical unit 68 is provided for recording an image of the right eye. The camera optical units 66, 68 may also have one or a plurality of lenses or other optical elements.

For image recording, the device in FIG. 6 includes beam splitters 64, 65. By means of the beam splitter 64, 65, the light from the eyes 610, 611 is directed to the image sensors 67 and 69, respectively. Light from the display 61 passes through the beam splitters 64, 65 to the eyes 610, 611. The beam splitters 64, 65 may be partly transmissive mirrors, for example.

In some embodiments, the first and second camera units may be coupled to the mobile computer device 60, for example wirelessly (for example via Bluetooth) or else in a wired fashion (for example via a USB connection or some other connection). In yet other embodiments, both the first and second camera units and the mobile computer device 60 may be controlled by an additional device (not illustrated).

As a result of two camera units 66-69 being provided, an examination of stereoscopic vision (both eyes jointly) may also be carried out besides the objective refraction determination for the eyes 610, 611.

Variations of the system will be described next with reference to FIGS. 7 to 12. In this case, as already explained, essentially the differences relative to FIG. 6 or to other figures described above will be discussed, and elements that remain the same will not be discussed again.

Figure 7:
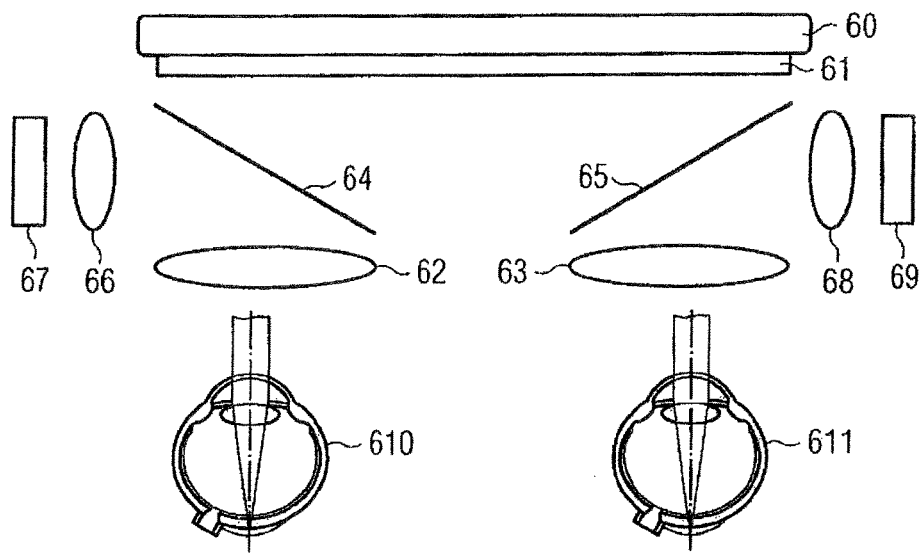
Figure 8:
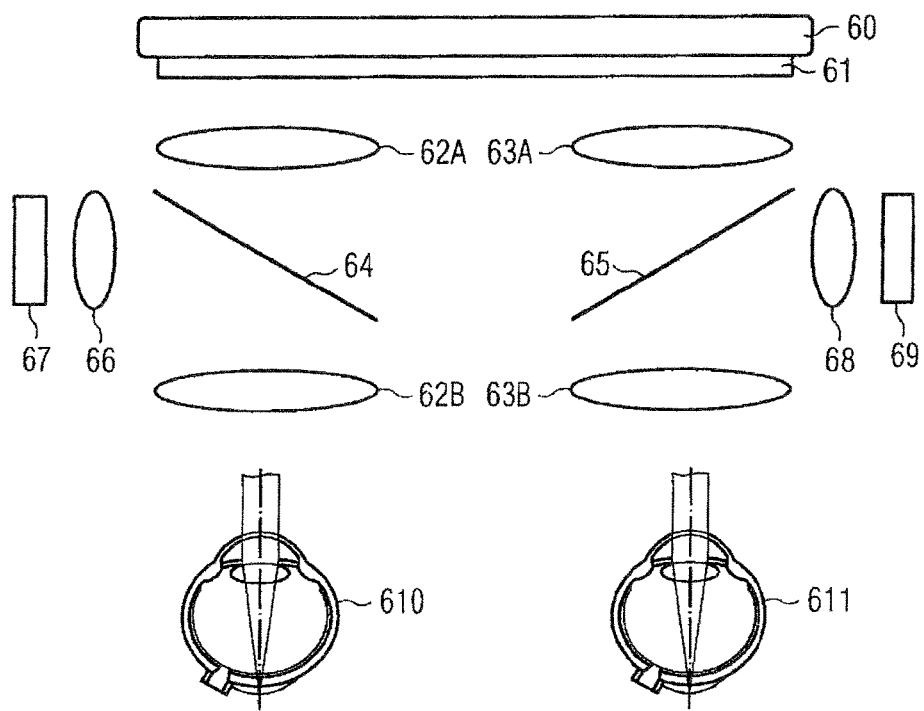

The position of the beam splitters 64, 65 is interchanged with the position of the optical units 62, 63 in FIG. 7 compared with FIG. 6. In FIG. 8, the optical units 62A, 62B for the optical unit 62 and the optical units 63A, 63B for the optical unit 63 are divided in two. The beam splitter 64 is arranged between the optical units 62A and 62B, and the beam splitter 65 is arranged between the optical units 63A and 63B. In some embodiments, the beam splitters 64 and 65 may also be arranged within lenses of the optical units 62, 63. In other words, FIGS. 6 to 8 show that the arrangement of the beam splitters 64, 65 and of the optical units 62, 63 is variable.

It should be noted that the optical units 62B, 63B may also be exchangeable, which, as will be explained later, may enable a subjective refraction determination.

In the embodiments discussed with reference to FIGS. 6-8, camera units (66-69) external to the mobile computer device 60 are used to record an image of the eyes 610, 611. In other embodiments, an internal camera of the mobile computer device 60 may be used for this purpose. Such an embodiment is illustrated in FIG. 9.

Figure 9:
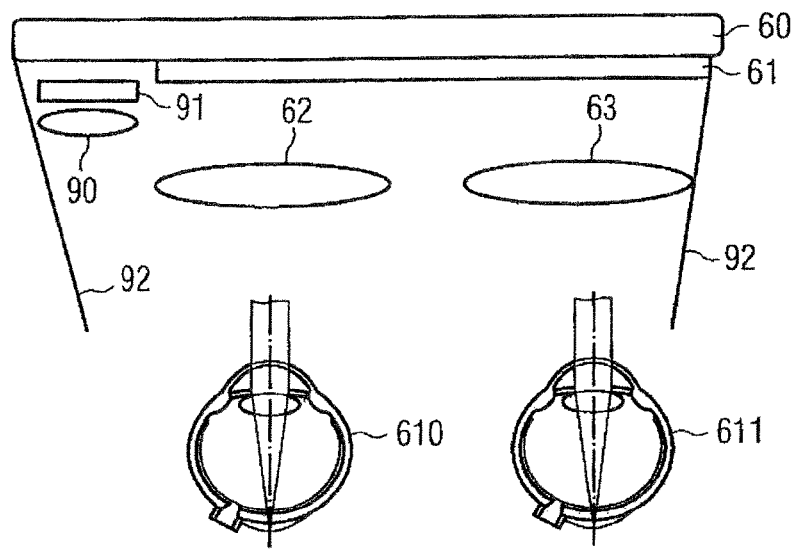

In the embodiment in FIG. 9, the mobile computer device 60 includes a camera unit having an image sensor 91 and a camera optical unit 90. The image sensor 91 may be for example a CMOS sensor or a CCD sensor. In the embodiment illustrated, a structured illumination of the eyes is again effected via the display 61 of the mobile computer device 60, and one or both eyes are recorded via the image sensor 91, in order thus to be able to carry out an objective refraction determination. 92 denotes a housing or the like which may prevent or reduce in particular the penetration of stray light.

Depending on the configuration of the camera unit 90, 91, it may be the case that only one eye (for example the eye 610 in FIG. 9) may be recorded. In this case, the alignment of the mobile computer device 60 must be reversed for example for determining the refraction of the eye 611. In other embodiments, additional optical elements (for example beam splitters) may be provided in order to direct light from the eye 611 to the image sensor 91. In other embodiments, the mobile computer device 60 may include two cameras.

In this case, by using an internal camera of the mobile computer device 60, the construction is simplified in so far as there is no need for an additional external camera device, if appropriate in association with optical elements such as beam splitters (for example 64, 65 in FIGS. 6-8). On the other hand, depending on the position of the camera, as explained above, only one eye may be recorded, which may possibly lengthen the eye examination. Moreover, in the case of a camera which can simultaneously record only one eye, it is not possible to measure stereoscopic vision as well.

Viewing optics 62, 63 of, for example, a head up display or of some other viewing device are used in the embodiments in FIGS. 6-9. Such viewing devices for smartphones are commercially available. Depending on the quality of the optical units 62, 63 and the structured illumination used, under certain circumstances the optical units 62, 63 may be inadequate to ensure a desired imaging of the illumination represented on the display 61 onto the eyes 610, 611.

Figure 10:
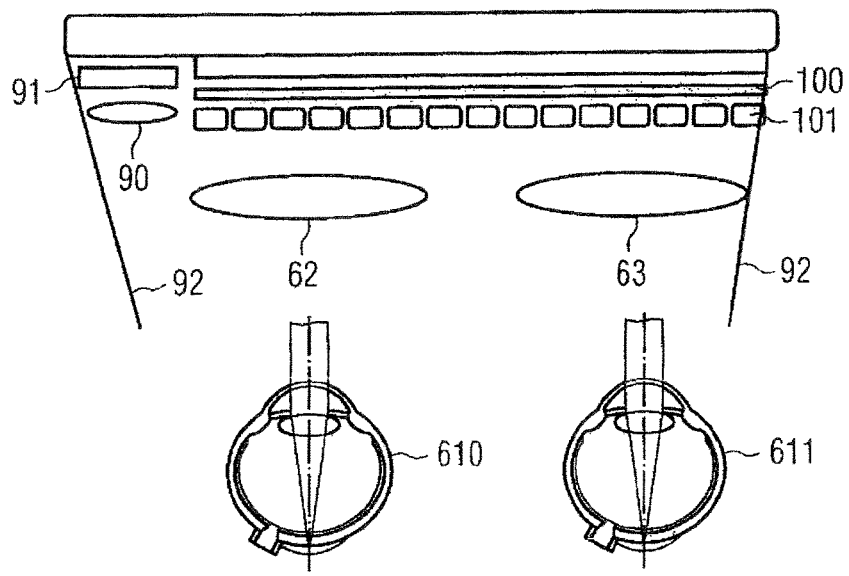

In this case, for example, as illustrated in FIG. 10, an additional microlens arrangement 101 may be provided upstream of the display 61. The microlens arrangement may ensure a desired imaging of the illumination represented on the display 61 (for example point light sources 42 in FIGS. 2, 4 or the ring segments 52 in FIG. 5) onto the eyes 610, 611. In one preferred embodiment, the microlens arrangement 101 is provided as a microlens film which may easily be adhesively bonded onto the display 61 or applied thereto in some other manner. In this way, the microlens arrangement 101 may be provided for an end user in a simple way.

In addition, in the embodiment in FIG. 10, the system illustrated includes a filter 100, which may likewise be provided as a film and is arranged between the display 61 and the microlens arrangement 101. Other arrangements are also possible. In some embodiments, the filter 100 may also be provided with the microlenses 101 in a single film, which may then be adhesively bonded onto the display 61 or applied thereto in some other manner. In this case, the filter 100 may be in particular a red and/or infrared filter which allows for example red light and/or infrared light to pass. The use of red light for the illumination of the eyes 610 and 611 may afford the advantage that this causes less narrowing of the eye pupil than with white light, for example, since the perceived brightness is lower. In other embodiments, the color of the illumination may be set directly via the display 61.

Figure 11:
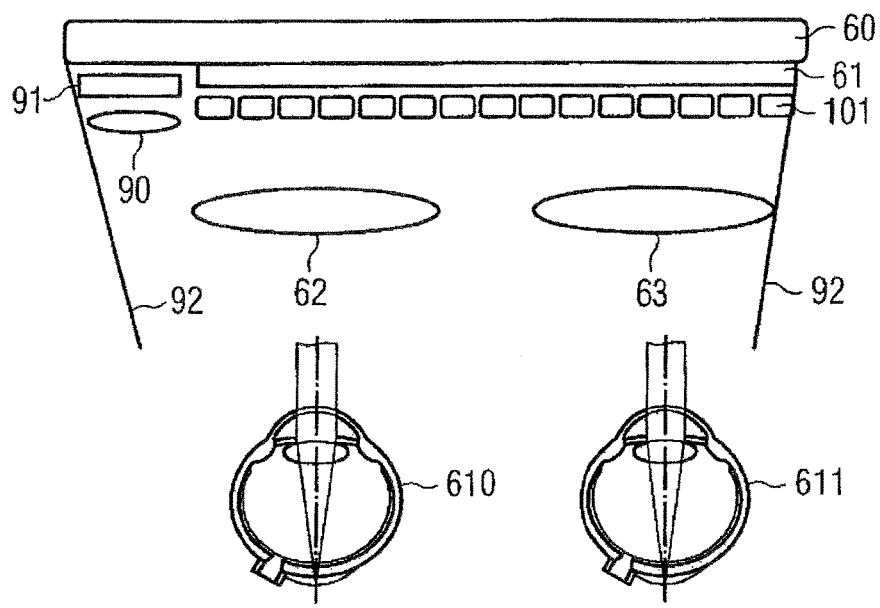

Consequently, the filter 100 may also be omitted, as is illustrated in the embodiment in FIG. 11. Apart from the omitted filter 100, the embodiment in FIG. 11 corresponds to the embodiment in FIG. 10.

In yet other embodiments, the microlenses 101 alone may already suffice to ensure an imaging of an illumination onto the eyes 610, 611. Such an embodiment is illustrated in FIG. 12.

Figure 12:
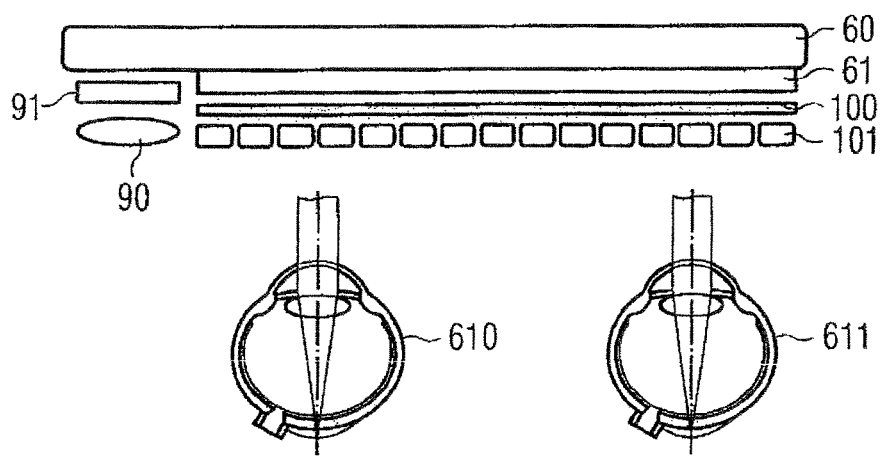

In the case of the embodiment in FIG. 12, only the filter 100 and the microlenses 101 are provided on the display 61. By contrast, the optical unit 62, 63 and the housing 92 are omitted, that is in this case the mobile computer device 60 may be provided for example without a head-mounted display or the like. In this case, for example, a user may be instructed to hold the mobile computer device 60 at a defined distance from his/her eyes 610, 611. In some embodiments, the correct alignment with respect to the eyes 610, 611 may also be controlled via the camera unit 90, 91.

By way of example, by means of a corresponding module such as the analysis module 16 in FIG. 1 a check may be made to ascertain whether the eyes have a desired position relative to the image sensor 91 or are imaged on the image sensor 91 in a desired size.

Other aids, such as a scale, may also be provided for positioning purposes. In the embodiment in FIG. 12, it is necessary to provide a user for example merely with a film having the filter 100 and the microlenses 101 for adhesive bonding onto the display 61 or application thereto in some other manner. In other embodiments, the filter 100 may also be omitted.

It should be noted that filter 100 and/or microlens film 101 may also be provided in the embodiments in FIGS. 6-9.

As evident from FIGS. 6-12, therefore, various systems and constructions are possible for obtaining an objective refraction determination by means of a mobile computer device such as a smartphone or a tablet. In this case, still other measurements, such as, for example, generally a sight/vision test, in particular also a stereoscopic test, may additionally be carried out.

Figure 13:
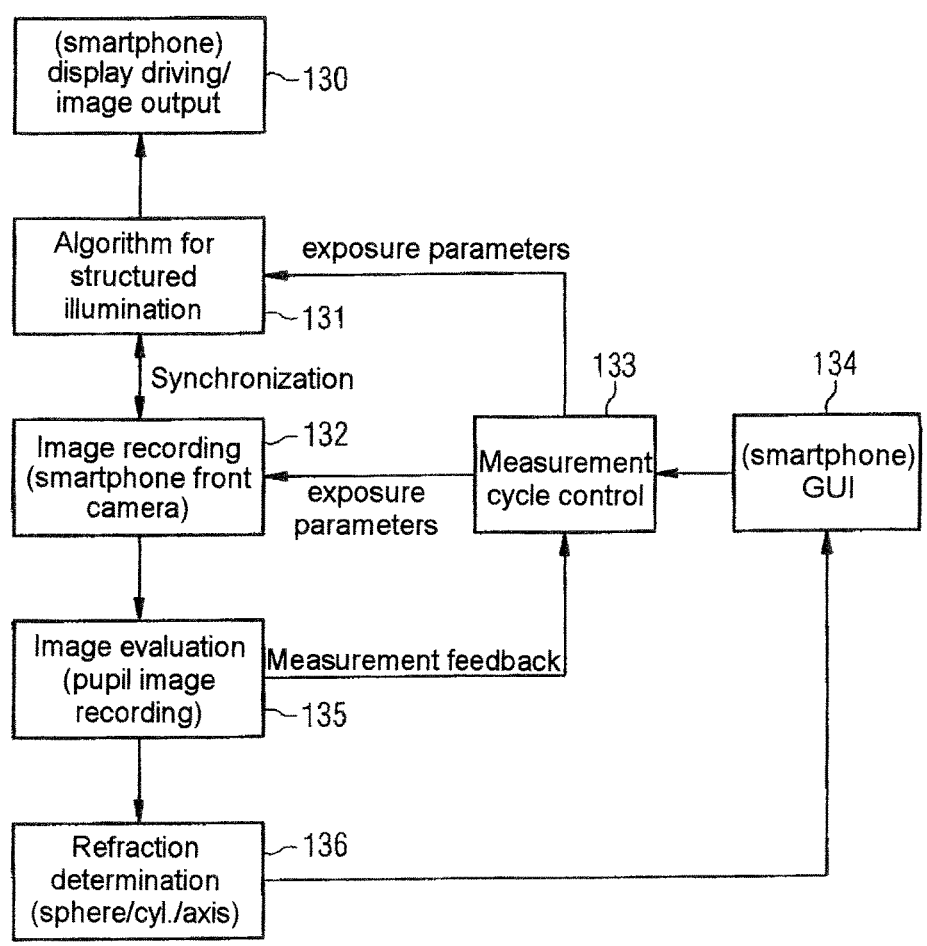
FIG. 13 is a block diagram for illustrating the functioning of systems for objective refraction determination in accordance with one embodiment.

A possible functioning of such systems for refraction determination is illustrated again in FIG. 13. In the illustration in FIG. 13, a smartphone is used as an example of a mobile computer device, but other mobile computer devices may also be used, for example tablet computers or mobile gaming devices. The different functionalities explained below with reference to FIG. 13 may be implemented for example by means of the above-described devices and systems, for example of a corresponding application on a smartphone. Consequently, the different blocks in FIG. 13 are not necessarily implemented as separate units, rather some of the blocks may also be implemented jointly by means of an application on a mobile computer device.

In this case, operation is carried out, as illustrated by a block 134, via a user interface of the mobile computer device, for example of the smartphone. Such a user interface may be in particular a graphical user interface, also referred to as GUI. In particular, a touch-sensitive display (so-called touch screen) may be used for this purpose. In particular, a measurement cycle control 133 which controls the refraction determination may be started and/or set by means of the user interface 134.

The measurement cycle control 133 transfers illumination parameters to an algorithm for structured illumination 131, which in turn drives an indicator, for example a display, of the mobile computer device in 130 in order to obtain a desired illumination. By way of example, an illumination as discussed with reference to FIG. 4 or 5 may be realized in this way. In this case, the illumination parameters may include for example a desired background brightness, a desired type of illumination (for example as illustrated in FIG. 4 or in FIG. 5) and the like. Moreover, the measurement cycle control 133 controls an image recording 132, for example by means of a front camera of a smartphone as illustrated in FIGS. 9-12 or else with one or a plurality of external cameras as illustrated in FIGS. 6-8. In this case, the measurement cycle control 133 may set in particular exposure parameters, for example exposure time, aperture and/or ISO value. In this case, in the embodiment in FIG. 13, the structured illumination 131 is synchronized with the image recording 132. By way of example, an image (or a plurality of images) can be recorded for each illumination direction (for example each point light source 42 in FIG. 4 and/or each circle segment 52 in FIG. 5).

In 135, an image evaluation of the image recorded in 132 is then effected. In this case, it is possible to evaluate in particular whether the recording of one or both pupils was effected correctly. On the basis thereof, a measurement feedback may be given to the measurement cycle control 133. On the basis of the measurement feedback, the illumination parameters and/or the exposure parameters may then be adapted. By way of example, in the case of a blurred image, the exposure time may be shortened, or a luminance may be increased if a pupillary light reflex to be evaluated is not visible.

In 136, a refraction determination is then effected on the basis of the recorded images.

In particular, the pupil back-reflection (optical passage of the light through the eye lens followed by a reflection at the retina and a second passage through the eye lens) may be evaluated in this case. By evaluating the gradient profile in the reflection image with a changing illumination direction, it is then possible to determine the defective vision of the eye (sphere, cylinder, axis) since the behavior of the back-reflection is dependent on these parameters.

In this case, systems as described above, by virtue of the fact that the mobile computer device is arranged relatively near to the eye to be measured or the eyes to be measured, may achieve a large field of view, that is the display of the mobile computer device may, in embodiments, fill a comparatively large part of the field of view, for example more than 50% or more than 70%. As a result, the "background illumination" may be set in accordance with a desired luminance adaptation level, and an arbitrary illumination pattern for the refraction determination may be set. Consequently, the optical refraction determination may be carried out by means of photo refraction with different pupil sizes in accordance with the different surround luminances. Particularly in systems in which the distance between the mobile computer device and the eye or eyes is clearly defined (for example with the use of a head-up display), in contrast to conventional handheld photorefraction meters, no distance measurement is necessary.

As already explained, an objective refraction determination is carried out in the embodiments discussed with reference to FIGS. 3-13. As already explained in the introduction, additionally or alternatively subjective refraction determinations may also be carried out with other embodiments. Such embodiments will now be explained with reference to FIGS. 14-17. Elements in FIGS. 14-16 which correspond to elements in FIGS. 6-12 once again bear the same reference signs and will not be explained in detail again. In particular, 60 once again denotes a mobile computer device such as a smartphone including a display 61, and 610 and 611 denote two eyes of a person to be examined. 62 and 63 denote viewing optics of a viewing device such as a head mounted display or the like.

140 and 141 denote changeable lenses or other changeable optical units, that is exchangeable lenses or other optical units. 143 denotes a mount for the exchangeable lenses 140, 141, for example a changeable frame. 142 denotes housing parts or other shadings which, on the one hand, shade ambient light and, on the other hand, provide separate light channels for the left eye 610 and the right eye 611. For the subjective refraction determination, characters, symbols or images are then represented on the display 61, and the person to be examined indicates whether, when the lenses 140, 141 are changed, for example, the image impression improves or deteriorates, and/or whether the person can recognize more or fewer symbols or characters.

As already explained, in some embodiments, both an objective refraction determination and a subjective refraction determination may be carried out. In such combined systems, for example, the lenses 62B and 63B in FIG. 8 may correspond to the lenses 140, 141 in FIG. 14. In this case, the subjective refraction determination may be carried out in particular separately for left eye 610 and right eye 611. However, a joint use of both eyes (for stereoscopic vision) is also possible. In any case it is helpful here if the light paths for left eye 610 and right eye 611 are separated as well as possible in order that no mutual interference is present. In other words, an image portion represented for the left eye 610 (for example from the region 21A in FIG. 2) should as far as possible pass only to the left eye 610, and an image portion represented for the right eye 611 on the display 61 (for example from the region 21B in FIG. 2) should as far as possible pass only to the right eye 611. Depending on the configuration, the separation by the housing 142 may be inadequate here. By way of example, in some head-up displays, the housing may not quite reach as far as the display 61, for example in order to enable the computer device 60 to be easily withdrawn from the housing. Additional measures may be implemented in such cases. Two possibilities in this respect will be explained with reference to FIGS. 15 and 16.

Figure 14:
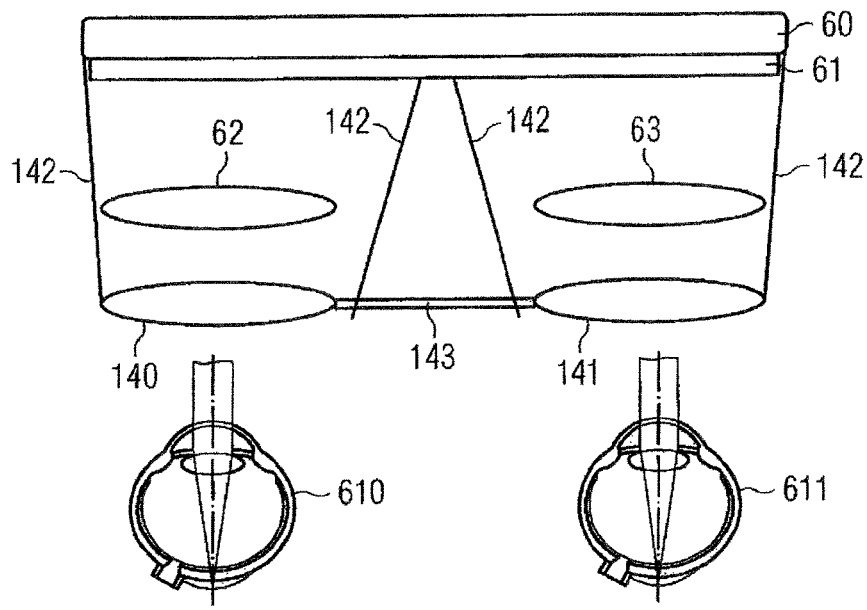
FIGS. 14 to 16 show systems for subjective refraction determination in accordance with various embodiments; and, FIGS. 17A to 17D show examples of screen representations for subjective refraction determination in accordance with embodiments.
Figure 15:
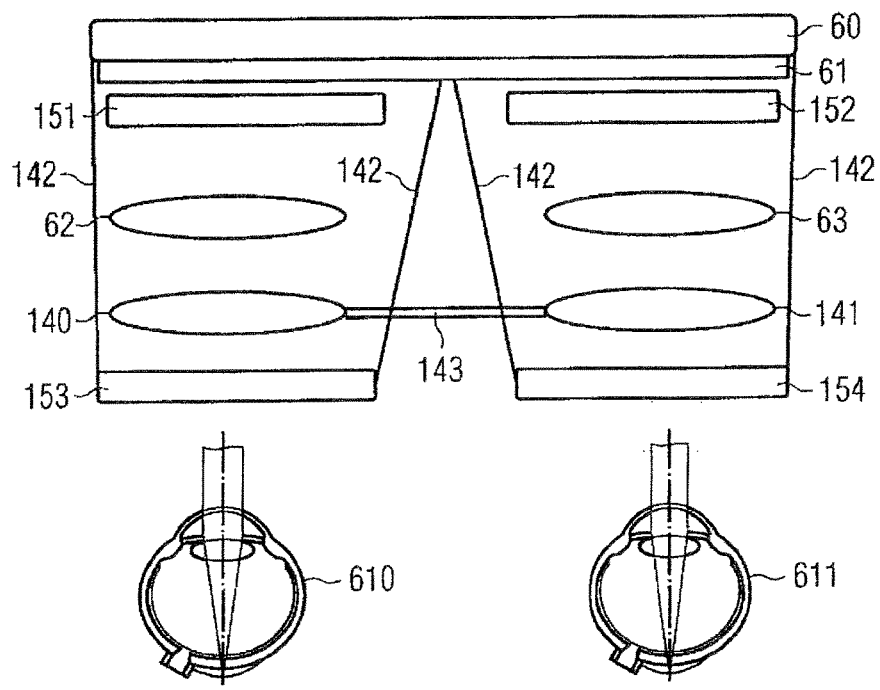
Figure 16:
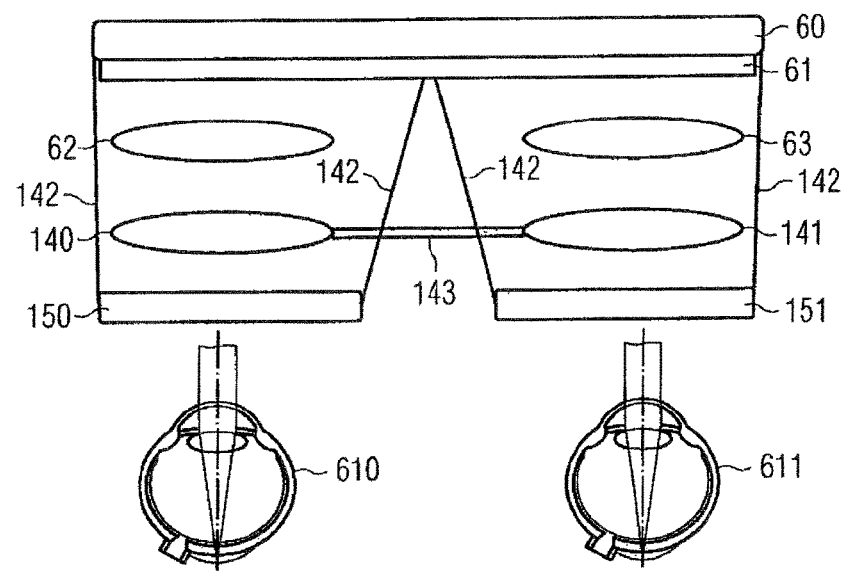
Figure 17A:
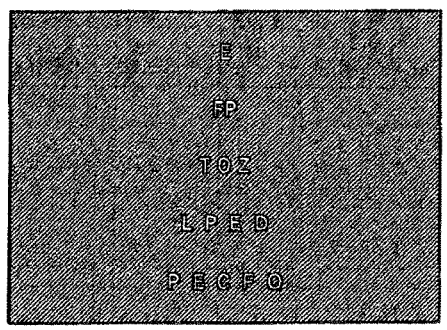
Figure 17B:
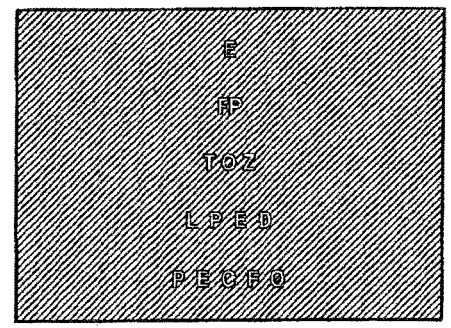
Figure 17C:
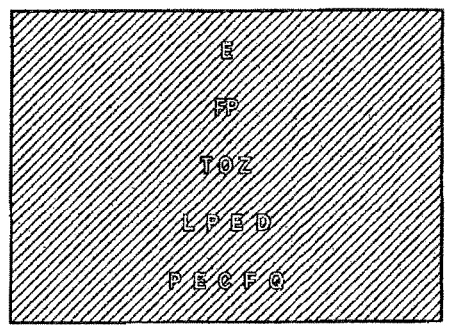
Figure 17D:
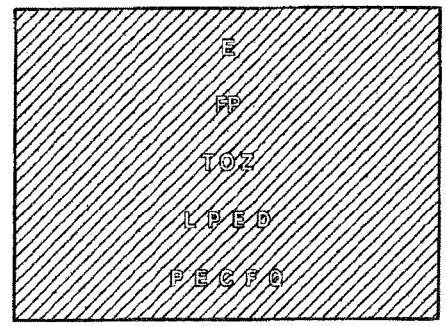

In this case, the systems in FIGS. 15 and 16 are based on the system in FIG. 14, and identical elements bear the same reference signs and will not be explained again.

In the case of the embodiment in FIG. 15, polarizers 151 and 152 are arranged above the display 61. The polarizers 151, 152 may have polarizations perpendicular to one another (for example left circular and right circular or two linear polarization directions perpendicular to one another).

In addition, analyzers 153, 154 are arranged at light exit locations of the housing 142. In this case, a polarization direction of the analyzer 153 corresponds to that of the polarizer 151. In a similar manner, a polarization of the analyzer 154 corresponds to a polarization of the polarizer 152. In some embodiments, an improved separation of the light paths for left and right eyes may be achieved in this way.

A further possibility is illustrated in FIG. 16. Shutters 160 and 161 for the left eye 610 and the right eye 611, respectively, are provided in the embodiment in FIG. 16. The shutters 160, 161 may be LCD shutters, for example. By means of the shutters 160, 161, the left and right eyes may be alternately darkened, and an image may be represented on the display 61 (for example in the corresponding region 21A or 21B in FIG. 2) at the same time only for the respectively non-darkened eye. In some embodiments, the change between left eye and right eye may take place so rapidly here that an image is represented simultaneously for both eyes. In this way, too, the separation of the light paths for the left eye 610 and the right eye 611 may be improved.

FIGS. 17A-17D illustrate various examples of letters which may be displayed for carrying out a subjective refraction determination. In this case, the size ratio of letters to background is not necessarily to scale, and in some embodiments the proportion of the background may be significantly larger in relation to the proportion of the letters. Moreover, the size of the letters may also vary from row to row, in contrast to the example in FIGS. 17A-17B. The person to be examined may then indicate, depending on changing lenses (for example the lenses 140 and 141), whether the letters are sharper or less sharp or are better discernible or less well discernible. In this case, FIGS. 17A-17D show varying surround luminances (Lu) and thus varying contrast between letters and background, whereby different lighting conditions and different types of vision (scotopic, mesopic, photopic) may be tested. In this case, the surround luminance, particularly if the respectively represented images fill a large part of the field of view (FoV), acts as adaptation luminances (La) which determine the eye adaptation. Such a field of view may be achieved for example by means of corresponding viewing optics, for example as discussed above. Additionally or alternatively, a brightness of the represented letters may be set in order to set a so-called infield luminance (Li). In this regard, the contrast between letters and background is greatest in FIG. 17A and least in FIG. 17D. In other embodiments, different colors may also be used in addition or as an alternative to different contrasts and brightnesses.

It should be noted that the result in the subjective refraction determination may differ from the result of the objective refraction determination. This is owing to the fact that the human brain may to a certain degree become accustomed to defective vision and may compensate for the latter. If eyeglasses which optically (objectively) exactly compensate for defective vision are then used, for example, the brain may nevertheless initially continue this compensation, which then worsens the subjective image impression again. In embodiments which enable both objective refraction determination and subjective refraction determination, for example both values may be communicated to medical specialist personnel, or a compromise from the results of the objective refraction determination and the subjective refraction determination may be used for example for an eyeglass or contact lens determination.

It is understood that the foregoing description is that of the preferred embodiments of the invention and that various changes and modifications may be made thereto without departing from the spirit and scope of the invention as defined in the appended claims.

In some embodiments, devices, methods, systems and computer program products in accordance with the following sections are provided:

Section 1. A mobile computer device, comprising:
  a display,
  a processor, and
  a memory with program code stored therein,
  wherein the program code, when it is executed on the processor, has the effect that the processor drives the display to display an image for determining the refraction of an eye on the display.

Section 2. The mobile computer device according to section 1, wherein the image comprises elements represented on a background, wherein a brightness of the background is settable for setting a surround luminance.

Section 3. The mobile computer device according to section 2, wherein an adaptation luminance is settable by setting the surround luminance.

Section 4. The mobile computer device according to section 2 or 3, wherein the brightness of the background is settable for selectively determining the refraction for at least two from the group comprising scotopic vision, photopic vision and mesopic vision.

Section 5. The mobile computer device according to any of sections 2-4, wherein a brightness of the elements is settable for setting an infield luminance.

Section 6. The mobile computer device according to any of sections 1-5, wherein the image comprises an image for the subjective refraction determination.

Section 7. The mobile computer device according to section 6, wherein the image comprises characters and/or symbols.

Section 8. The mobile computer device according to any of sections 1-7, wherein the image comprises a structured illumination for illuminating the eye for an objective refraction determination.

Section 9. The mobile computer device according to section 8, wherein the structured illumination is temporally variable in order to illuminate the eye from different directions.

Section 10. The mobile computer device according to section 8 or 9, wherein the structured illumination comprises selectively drivable, circularly arranged light source points or ring segments.

Section 11. The mobile computer device according to any of sections 8-10, further comprising a camera unit for recording a pupillary light reflex in response to the structured illumination.

Section 12. The mobile computer device according to any of sections 1-11, wherein the mobile computer device comprises an interface for coupling to an external camera and for receiving a recorded pupillary light reflex in response to the structured illumination from the external camera.

Section 13. The mobile computer device according to section 11 or 12, wherein the program code, when it is executed on the processor, carries out a determination of the refraction of the eye on the basis of the recorded pupillary light reflex.

Section 14. A system, comprising:
  a mobile computer device according to any of sections 1-13, and
  viewing optics for viewing the mobile computer device with at least one eye of a person to be examined.

Section 15. The system according to section 14, wherein the viewing optics comprise a first optical unit for a first eye and a second optical unit for a second eye.

Section 16. The system according to section 14 or 15, wherein the viewing optics comprise a microlens arrangement.

Section 17. The system according to section 16, wherein the microlens arrangement comprises a microlens film to be fitted on the display of the mobile computer device.

Section 18. The system according to any of sections 14-17, wherein the viewing optics comprise a color filter.

Section 19. The system according to section 18, wherein the color filter comprises a red filter and/or infrared filter.

Section 20. The system according to any of sections 14-19, further comprising a beam splitter arranged between the display of the mobile computer device and the at least one eye, wherein the beam splitter is arranged to direct light emerging from the eye to a camera unit.

Section 21. The system according to any of sections 14-20, further comprising a changeable mount for a changeable optical unit for the subjective refraction determination.

Section 22. The system according to any of sections 14-21, further comprising, for at least one eye, a combination of polarizer and analyzer.

Section 23. The system according to any of sections 14-22, further comprising, for at least one eye, a shutter.

Section 24. A computer program product comprising a program code,
  wherein the program code, when it is executed on a processor, has the effect that the processor drives a display to display an image for determining the refraction of an eye on the display.

Section 25. The computer program product according to section 24, wherein the computer program product is configured for implementing a mobile computer device according to any of sections 1-13.

As already explained, the above embodiments are intended only for illustration purposes, and should not be interpreted as restrictive. Variants and modifications that were discussed with regard to the objective refraction determination may, if appropriate, also be used in the subjective refraction determination. By way of example, a microlens film for imaging may also be provided for the subjective refraction determination. Other variations are also possible.

What is claimed is:

1. A system for determining subjective refraction of the eye or eyes of a person, the system comprising:
   a mobile computer device having a display, a processor, and a non-transitory computer-readable medium having program code stored therein;
   said program code, when executed on the processor, causing said processor to drive said display to display an image thereon for determining the subjective refraction of an eye;
   said image including a background and elements shown thereon;
   said background of said image defining a first brightness, wherein said first brightness of said background is configured to be settable for setting a surround luminance;
   said first brightness of said background of said image being configured to be settable independently of a second brightness of said elements and to be selectively settable to one of at least two different predefined brightness values;
   said at least two different predefined brightness values of said first brightness being from a group including a first predefined brightness value in a range of scotopic vision with a first luminance of less than 0.03 cd/m$^2$, a second predefined brightness value in a range of photototopic vision with a second luminance of greater than 3 cd/m$^2$ and a third brightness value in a range of mesopic vision with a third luminance between said first luminance and said second luminance so as to permit the determination of the refraction of the eye to be carried out in different ranges of vision;
   viewing optics for viewing said mobile computer device with at least one eye of a person to be examined; and,
   said viewing optics including a first optical unit for a first eye and a second optical unit for a second eye to facilitate determination of said subjective refraction.

2. The system of claim 1 further comprising a combination of polarizer and analyzer for at least one eye.

3. The system of claim 1, wherein said viewing optics include a microlens arrangement.

4. The system of claim 1, wherein said viewing optics include a microlens film to be fitted on said display of said mobile computer device.

5. The system of claim 1, wherein said viewing optics include at least one of a color filter, a red filter, and an infrared filter.

6. The system of claim 1, further comprising a beam splitter arranged between the display of the mobile computer device and the at least one eye, wherein the beam splitter is arranged to direct light emerging from the eye to a camera unit.

7. The system of claim 1 further comprising a shutter for at least one eye.

* * * * *

UNITED STATES PATENT AND TRADEMARK OFFICE
CERTIFICATE OF CORRECTION

Page 1 of 1

PATENT NO. : 10,182,717 B2
APPLICATION NO. : 15/430514
DATED : January 22, 2019
INVENTOR(S) : K. Lindig et al.

It is certified that error appears in the above-identified patent and that said Letters Patent is hereby corrected as shown below:

In the Specification

In Column 2:
Line 45: delete "photoptic" and substitute -- photopic -- therefor.

In Column 10:
Line 64: delete "L u" and substitute -- L_u -- therefor.

In Column 11:
Line 26: delete "phototopic" and substitute -- photopic -- therefor.

In the Claims

In Column 20:
Line 1: Claim 1, delete "totopic" and substitute -- topic -- therefor.

Signed and Sealed this
Twenty-fifth Day of June, 2019

Andrei Iancu
*Director of the United States Patent and Trademark Office*